United States Patent
Schneider et al.

(10) Patent No.: US 6,639,964 B2
(45) Date of Patent: Oct. 28, 2003

(54) DEVICE AND METHOD FOR FORMING A COMPUTED X-RAY TOMOGRAM WITH SCATTER CORRECTION

(75) Inventors: Stefan Schneider, Aachen (DE); Josef Lauter, Aachen (DE); Herfried Karl Wieczorek, Aachen (DE); Olaf Such, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 155 days.

(21) Appl. No.: 09/963,300

(22) Filed: Sep. 26, 2001

(65) Prior Publication Data

US 2002/0048339 A1 Apr. 25, 2002

(30) Foreign Application Priority Data

Sep. 27, 2000 (DE) .......................................... 100 47 720

(51) Int. Cl.[7] .............................................. G01N 23/00
(52) U.S. Cl. ................................ 378/7; 378/70; 378/86
(58) Field of Search ............................ 378/1, 4, 7, 21, 378/70, 86, 87, 88, 89, 90

(56) References Cited

U.S. PATENT DOCUMENTS

| | | | | |
|---|---|---|---|---|
| 4,995,107 A | * | 2/1991 | Klingenbeck | 378/7 |
| 5,327,476 A | * | 7/1994 | Kemner | 378/98.4 |
| 5,463,666 A | | 10/1995 | Eberhard et al. | 378/4 |
| 5,615,279 A | | 3/1997 | Yoshioka et al. | 382/131 |
| 5,905,809 A | * | 5/1999 | Timmer | 382/131 |
| 5,930,326 A | * | 7/1999 | Rothschild et al. | 378/57 |
| 6,173,033 B1 | * | 1/2001 | Klingenbeck-Regn et al. | 378/20 |
| 2001/0002699 A1 | * | 6/2001 | Such et al. | 250/367 |
| 2001/0011701 A1 | * | 8/2001 | Such et al. | 250/250 |
| 2002/0141541 A1 | * | 10/2002 | Darboux et al. | 378/210 |
| 2003/0103666 A1 | * | 6/2003 | Edic et al. | 382/132 |
| 2003/0138074 A1 | * | 7/2003 | Bruder | 378/4 |

FOREIGN PATENT DOCUMENTS

| | | | | |
|---|---|---|---|---|
| DE | 19721535 A | 11/1998 | | A61B/6/08 |
| DE | 19844543 A | 4/1999 | | G06T/17/00 |

* cited by examiner

*Primary Examiner*—Eric S. McCall
(74) *Attorney, Agent, or Firm*—John Vodopia

(57) ABSTRACT

The invention relates to a method for scatter correction while forming a computed X-ray tomogram. The distribution of the scattered radiation is determined by detector cells (7') which, because of the measuring method carried out, are shielded from direct irradiation in a two-dimensional, multi-cell detector field (3). This distribution is used to perform a scatter correction in the neighboring, directly irradiated detector cells (7). Furthermore, scatter correction can be performed by computer simulation of the scatter processes. To this end, use is preferably made of a Monte Carlo method and the effect of the geometry and the material composition of the measuring arrangement, of the patient size, of the irradiated tissue and the like, is taken into account.

20 Claims, 3 Drawing Sheets

DEVICE AND METHOD FOR FORMING A COMPUTED X-RAY TOMOGRAM WITH SCATTER CORRECTION

FIELD OF THE INVENTION

The invention relates to a method of forming a computed X-ray tomogram of an object which is irradiated in a measuring device that consists of an X-ray source and a detector field, the radiation intensity measured in the detector field being subjected to scatter correction. The detector field may notably be a two-dimensional multi-cell field, a part of which that is not bounded at right angles is shielded from direct irradiation by the X-ray source. The invention also relates to an X-ray computed tomography apparatus which includes a measuring device with an X-ray source and a detector field, as well as a correction unit for performing a scatter correction on the radiation intensity measured in the detector field. The invention notably relates to an X-ray computed tomography apparatus in which the detector field is a two-dimensional multi-cell field which includes shielding means that are arranged in such a manner that they shield a part of the detector field that is not bounded at right angles.

BACKGROUND OF THE INVENTION

In order to form a computed tomogram, an object to be examined, notably the body of a patient, is irradiated by X-rays from an X-ray source and the radiation having traversed the object is detected in respect of its radiation intensity in a detector field on the other side of the object. For the formation of a cross-sectional image of the irradiated object, the absorption of the X-rays during their travel through the object, and hence also the optical density (measured in Hounsfield units) or the material composition of the object, are established on the basis of the radiation intensity measured in the detector field.

The (primary) radiation that directly traverses the object is responsible for generating the desired imaging information. However, in addition processes of scattering of the photons of the X-rays also occur in the object; during these processes the photons change their direction and possibly their energy. Part of the scattered radiation also reaches the detector and contributes to the radiation intensity measured thereby. However, because the scattered radiation does not reach the detector along a direct path from the radiation source, it does not contribute to the useful image information but is superposed instead on the information that can be derived from the direct radiation.

Because in a first approximation the scattered radiation increases linearly as a function of the irradiated volume of the object, its disturbing effect is greater as the slice thickness irradiated in the computed tomography (CT) apparatus is greater. Whereas nowadays slice thicknesses of from 0.8 to 3 mm are customarily examined in computed tomography apparatus, there is a growing tendency towards the use of multi-line computed tomography apparatus with a slice thickness of approximately 2 cm or even more. Consequently, the background due to scattered radiation and the associated deterioration of the image quality will increase.

Various methods are known for the reduction of the disturbing effects of the scattered radiation. For example, on the one hand it can be attempted to prevent the scattered radiation from reaching the detector in the first place. These methods utilize the sole relevant difference between primary photons and scattered photons, that is, the difference in the distribution of their angle of incidence. Whereas all primary photons arrive from the radiation source along a straight path, scattered photons have "oblique" angles of incidence that deviate therefrom. Therefore, it is known to utilize so-called anti-scatter grids (ASG) which consist of thin foils of a high-grade absorbing material such as, for example molybdenum or tungsten and are arranged so as to be aligned with the focal point of the X-ray anode. Therefore, the ASG suppresses primary photons only if they are incident on an end face of the foils whereas scattered photons are absorbed upon incidence on the foil surface. For computed tomography applications the suppression factor for the scattered radiation can thus readily reach high values of from 10 to 20. The primary radiation, however, is reduced by only a factor of from approximately 1.1 to 1.3. The anti-scatter grids, however, have the drawback that their manufacture is very expensive and that their application is highly complex. Furthermore, it is questionable whether the suppression factors achieved will indeed be adequate for future large slice thicknesses.

Moreover, scatter correction is normally performed by subtracting a constant scattered radiation background, conservatively estimated on the basis of the object size, from the measuring values. Image artefacts such as stripes and so-called pockets, however, remain visible.

U.S. Pat. No. 5,615,279 discloses a method for scatter correction in a computed tomography apparatus in which first measurements of the scattered radiation are performed on model bodies (phantoms) of different thickness, the measuring results being taken up in a table. When computed tomograms are formed from real patients, correction values are calculated for the measuring data, while taking recourse to the stored tables, in order to reduce the effect of the scattered radiation as much as possible. This method has the drawback that a large amount of experimental work is required for composing the tables with the correction values. Because of this large amount of work, usually only a few parameters that have an effect on the scattered radiation can be varied. Notably the object size of the phantom is one of these parameters.

Furthermore, DE 197 21 535 A1 discloses an X-ray computed tomography apparatus in which the detector field is formed by a plurality of adjacently situated rows that consist of concatenated detector cells. The measuring device, consisting of the X-ray source and the detector field as well as collimators, can be displaced relative to the longitudinal axis of the patient. The plurality of rows of the detector field are arranged so as to extend perpendicularly to the axis of displacement and parallel to one another, so that different slices of the body are successively imaged on the detector cells during a relative displacement between the measuring arrangement and the patient. The collimators can notably be adjusted in such a manner that the detector rows that are situated at the edge of the detector field are shielded from direct irradiation by the X-ray source. Consequently, only scattered radiation can be incident on these rows, so that the measuring signal acquired in these row forms an indication of the extent of the scattered radiation; this indication can be used for scatter correction of the primary measuring values. This arrangement has the drawback that specific rows of the detector field must be reserved for the scatter correction.

SUMMARY OF THE INVENTION

Considering the foregoing it is the object of the present invention to provide a method of generating an X-ray computed tomogram as well as an X-ray computed tomography apparatus which both enable improved scatter correction.

This object is achieved by means of a method in conformity with the characteristics of claim 1, by means of a method in conformity with the characteristics of claim 10, by means of an X-ray computed tomography apparatus in conformity with the characteristics of claim 7 as well as by means of an X-ray computed tomography apparatus in conformity with the characteristics of claim 18. Advantageous further embodiments are disclosed in the dependent claims.

According to a first version of a method in accordance with the invention for forming an X-ray computed tomogram of an object, notably the body of a patient, the object is irradiated in a measuring arrangement that consists of an X-ray source and a detector field and the radiation intensity measured in the detector field is subjected to scatter correction. The detector field is then conceived so as to be a two-dimensional multi-cell field, meaning that the individual cells of the detector are adjacently arranged in rows and columns in the form of a matrix. Not all cells need have the same geometrical size.

Furthermore, in accordance with the above method a part of the detector field which is not bounded at right angles is shielded from direct irradiation by the X-ray source. Shielding of this kind occurs in various methods for forming a computed tomogram where, for example, because of a special relative motion between the measuring arrangement and the object, the measuring signals must be evaluated at the detector end in a region that is not bounded at right angles. An example of such a method is a helical scanning of the object where the measuring arrangement rotates around the object while progressing along a helical path along the axis of the object. In the case of such methods, the part of the detector field that is relevant for the evaluation of the X-ray exposure assumes complex shapes which are not simply bounded at right angles (see U.S. Pat. No. 5,463,666 and DE 198 44 543 A1).

In such a method in accordance with the invention for forming an X-ray computed tomogram the radiation intensity is also measured within the shielded part of the detector field and used for scatter correction of the measuring values in the directly irradiated part of the detector field. Consequently, as opposed to customary methods, the signal from the shielded part of the detector field is not rejected. Because no direct primary radiation is incident on the shielded part of the detector field, this part does not contribute to the actual image information. The radiation intensity measured in this part originates exclusively from scattered radiation. The measuring values in this part, therefore, may form an indication of the local magnitude of the scattered radiation, so that they can be advantageously used for the correction of the actual measuring values from the directly irradiated part of the detector field. For this scatter correction it is not necessary to provide additional rows in the detector field. The already present rows of the detector fields that are not directly irradiated because of the relevant shielding are used to provide the desired information concerning the scattered radiation.

The shielded part of the detector field is bounded at least partly by curved lines. For various methods for X-ray computed tomography such a curved boundary is obtained because of the relative motion of the measuring arrangement and the object.

In accordance with a further version of the method, the scatter correction takes into account only those cells of the shielded part of the detector field that are shielded completely, that is, across their entire surface area. Generally speaking, the cells of the detector field are arranged at right angles or as squares in a regular grid in the detector field. However, the part of the detector field which is shielded from direct irradiation by the X-ray source by way of a relevant arrangement of shielding means, is bounded by sides that do not extend at right angles to one another or by sides that are even curved. Consequently, the edges of the shielded surface of the detector field usually extend right through the relevant cells of the detector field. These cells, therefore, are situated partly in the shielded region and partly in the directly irradiated region Moreover, there is a penumbra that is caused by the finite dimensions of the X-ray source. The cells of the detector that are situated at the boundary between the shielded part and the non-shielded part of the detector field, therefore, usually deliver a signal that cannot be unambiguously attributed to the one or to the other part. Therefore, in order to avoid measuring errors, the signals from these detector cells, that is, cells which are not fully shielded, are preferably not taken into account for the scatter correction.

In conformity with a further version of the invention, the radiation intensity averaged across two or more cells in the shielded part of the detector field is used for the scatter correction. Because the magnitude of the scattered radiation generally varies in a low-frequency manner, that is, only slowly in space, the signals from a plurality of cells in the shielded part of the detector field are advantageously combined so as to form an averaged signal therefrom. The values for the scattered radiation can thus be smoothed and incorrect interpretations due to incidental fluctuations can be avoided.

The scatter correction at a point in the directly irradiated part of the detector field can be performed by subtracting from the measuring value of this point the radiation intensity that was measured in the cell of the shielded part of the detector field that is nearest to the point in question. Alternatively, two or more cells in the shielded part of the detector field can be combined so as to form the mean value of their measuring signals, the cells used for this purpose being the cells that are situated nearest in space to the point in question in the directly irradiated part of the detector field. Finally, it is also possible to take into account the scattered radiation measured in the entire shielded part of the detector field by interpolation or extrapolation for the scatter correction in a point. To this end, for example, the parameters for a mathematical model of the scattered radiation distribution that covers the entire detector field can be adapted by means of the values measured in the shielded part.

Because the distribution of the scattered radiation in the shielded part of the detector field possibly deviates slightly from that in the non-shielded part, the scatter correction advantageously utilizes a calibration factor which compensates this difference. The calibration factor can be comparatively simply determined experimentally or estimated theoretically. The calibration factor can also take into account the locally different space angles at which scattered radiation may be incident.

Preferably, the measuring arrangement is displaced along a helical trajectory around the axis of the object during the formation of a computed tomogram. Such a method enables continuous formation of the computed tomogram with a reduced radiation load for the patient. As a result of this special exposure mode, only a part of the detector field that is not bounded at right angles will be required for the evaluation and formation of the image. The part of the detector field that is not required, therefore, is shielded by suitably shaped collimators in order to minimize the radiation load for the patient. Such an arrangement contains shielded parts of the detector field that have not been used thus far and are now available for scatter correction in accordance with the invention.

The invention also relates to an X-ray computed tomography apparatus which includes
- a measuring arrangement which consists of an X-ray source and a two-dimensional multi-cell detector field, the measuring device preferably being displaceable in one direction,
- shielding means which are arranged in such a manner that they shield a part of the detector field that is not bounded at right angles, and
- a correction unit for scatter correction of the radiation intensity measured in the detector field.

The X-ray computed tomography apparatus in accordance with the invention is characterized in that the correction unit is coupled to the shielded part of the detector field and is arranged in such a manner that it utilizes the radiation intensity measured in this part for the scatter correction. Evidently, the correction unit may also be coupled to the entire detector field; in that case, however, it utilizes the radiation intensity measured in the shielded part for the scatter correction in accordance with the invention. The advantages of the described method can be achieved by means of such an X-ray computed tomography apparatus. These advantages include notably an improvement of the image quality by way of a scatter correction which measures the actual magnitude of the scattered radiation in a locally resolved manner while utilizing shielded parts of the detector field. The scatter correction that can be achieved by means of the device is significantly better than that offered by the customary subtraction of an estimated constant value for the scatter background.

Preferably, the correction unit of the X-ray computed tomography apparatus is arranged in such a manner that it is capable of carrying out the various versions of the method described above. It may notably be arranged in such a manner that it takes into account only fully shielded cells of the detector fields for the scatter correction, that it averages the measuring values from a plurality of neighboring cells of the detector field and takes into account these mean values for the scatter correction, and/or that it performs a scatter correction at a point in the directly irradiated part of the detector field by subtraction of an interpolated/extrapolated scatter intensity (for example, that which occurs in the next cell or on average in a plurality of nearest cells in the shielded part of the detector field).

The correction unit in a further embodiment of the X-ray computed tomography apparatus in accordance with the invention is coupled to the shielding means in such a manner that the shielding means provide the correction unit with information signals concerning the shape and magnitude of the shielded region of the detector field. Such a coupling makes sense notably when the shielding of the detector field changes as a function of the scanning method carried out or in dependence on other secondary parameters. In that case the correction unit can receive the instantaneous and actual shape and magnitude of the shielded part of the detector field automatically from the shielding means, so that it can take into account the appropriate cells of the detector field for the scatter correction.

The invention also relates to a method of forming an X-ray computed tomogram of an object where the object is irradiated in a measuring arrangement that consists of an X-ray source and a detector field and the radiation intensity measured in the detector field is subjected to scatter correction. The method is characterized in that the scatter correction takes into account the results of a computer simulation of the scatter processes.

The scatter correction that can be achieved by means of the method in accordance with the invention is substantially better than that enabled by the customary subtraction of a constant scatter background. As opposed to the method that is known from U.S. Pat. No. 5,615,279, no intricate experiments are required for the determination of the scatter; instead the magnitude of the scatter arising can be determined with a high accuracy and while taking into account a large number of parameters in a computer simulation. This also offers the advantage that, should parameters change, for example, a different geometrical configuration of the measuring arrangement, the computer simulation can be readily performed while using other secondary parameters, thus enabling a flexible response to such changes.

The computer simulations of the scatter processes are preferably performed by means of a Monte Carlo method. According to such a method the trajectories of numerous virtual photons are calculated and followed during the simulation. The Monte Carlo method is based on the calculation of random quantities which determine, for example, changes of direction of the virtual photons and decide whether a photon is absorbed or scattered. Among these random variables the distribution functions and/or distribution densities are known and applied accordingly. The treatment of radiation transport problems by means of the Monte Carlo method is known in principle from astrophysics and from nuclear physics, so that these fields can be referred to for fundamental theoretical details. After calculation of an adequate number of individual photon paths, a distribution of the scattered photons incident on the detector is obtained, which distribution corresponds approximately to the actual distribution occurring.

During the computer simulation of the scatter processes notably the geometry and the material properties of the measuring arrangement (X-ray source, collimators and detector fields), of the patient table and of other objects possibly involved in scatter processes are taken into account. The geometry and the material properties of these objects are exactly known. The parameterized acquisition of these variables in the computer simulation enables, in response to a change of construction, calculation of an adapted scatter correction, by repeating the simulation with the changed data.

Furthermore, the computer simulation preferably takes into account the geometry and the material properties of a model of the patient body in the irradiated zone. The dependency of the scattered radiation on the types of tissue examined, for example the center of the brain, liver, hips etc., can thus be determined. The scattered radiation can in principle also be determined in dependence on internal structures of the body, for example the distribution of the bones. Because of the low-frequency behavior of the scattered radiation, such structures are usually evened out to such an extent that they are no longer recognizable in the image. Said computer simulations by means of a model of the patient body are preferably performed for different sizes of the model, so that the data acquired by means of a corresponding model can be used for the later examination of a patient. The results of the computer simulation in particular can then also be adapted to the exact size of the patient by multiplication by at least one suitable scaling factor.

Furthermore, the computer simulation can take into account the interaction between the scattered radiation and the detector. Generally speaking, the sensitivity of response of the detector or scintillator differs for photons of different energies. The disturbing effect exerted on the signal of a detector cell by the scattered photons is thus dependent on the energy of these photons. A detailed computer simulation model, therefore, also takes into account the energy at which the scattered photons are incident on the detector and also the signal produced thereby in the detector.

Furthermore, the model used in the computer simulation can be improved by also taking into account backscattering of photons from the (half) space which is situated behind the detector field (viewed from the radiation source). Photons that have passed through or have missed the detector field can be diverted back to the detector field by scatter processes that subsequently take place in the backspace and hence cause a signal in the detector field as yet. The computer simulation, therefore, can be improved by taking into account also such contributions by backscattered photons.

The results of the computer simulations are preferably stored in a look-up table for various secondary parameters which concern notably the geometry of the measuring arrangement, the measuring method used and the object size. The relevant data, such as notably the calculated magnitude of the scattered radiation at a given point in the detector field, can be readily fetched from such tables. For such fetching, the parameters involved in the current measurement, for example the patient size, can be considered so as to revert to the respective relevant data.

The invention also relates to an X-ray computed tomography apparatus which includes a measuring arrangement with an X-ray source and a detector field, as well as a correction unit for scatter correction of the radiation intensity measured in the detector field. The X-ray computed tomography apparatus is characterized in that the correction unit is arranged to carry out a method of the kind set forth. This means that the correction unit takes into account the results of a computer simulation of the scatter processes for the scatter correction. When the correction unit is provided with an appropriate computer capability, this computer simulation can be performed by the correction unit itself. The computer simulation, however, is preferably executed separately (off-line) by means of suitable computers, only the results of the computer simulation being presented to the correction unit in the form of tables or the like. The results can then take into account the effects of various secondary parameters such as the geometry and the material properties of the measuring arrangement, of the patient table, the surroundings, a model of the patient body and the like.

The correction unit preferably includes a memory for storing a look-up table in which the results of at least one computer simulation are stored. Preferably, the look-up table stores the results of several computer simulations, the individual simulations deviating from one another in respect of the variation of one parameter such as, for example the size of the patient model. In a concrete situation involving the formation of a computed tomogram, the correction unit can then specifically access the appropriate computer simulation in the lookup table.

The correction unit is preferably implemented as at least one digital signal processor (DSP). Digital signal processors have been optimized for fast execution of signal conversions. A system comprising a plurality of DSPs can nowadays reach data rates of approximately 1 Gbit/s. Up to 100 one-dimensional scatter distributions can be stored in the internal memory of a DSP. Because the access times to external memories are about as short as those for internal memories, moreover, an increased number of distributions can be stored in look-up tables in the external memory without affecting the real-time processing of the measured profiles. It is also possible to link two, four or more DSPs so as to achieve a greater capability.

BRIEF DESCRIPTION OF THE DRAWINGS

The invention will be described in detail hereinafter, by way of example, with reference to the Figures. Therein.

DETAILED DESCRIPTION OF THE PREFERRED EMBODIMENTS

Figure 1:
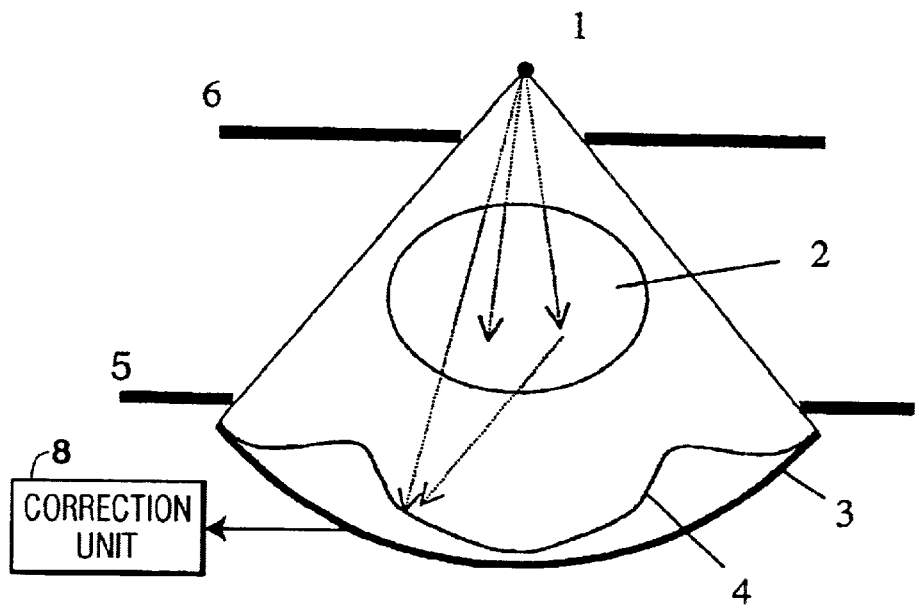
FIG. 1 illustrates the formation of a computed tomogram in the form of a diagrammatic cross-sectional view.

FIG. 1 shows diagrammatically the situation during the formation of a computed tomogram. X-rays are emitted by an X-ray source 1 in a sector which is bounded by the collimators 6 arranged near the radiation source 1. The collimators 6 serve notably to limit the beam in the direction perpendicular to the plane of drawing. The thickness of the irradiated sector (perpendicular to the plane of drawing) typically amounts to from 0.8 to 3 mm; however, in future larger slice thicknesses of up to 2 cm are expected to be pursued. The X-rays subsequently traverse an object 2 to be examined, for example the body of a patient. A detector field 3 which is sensitive to X-rays is arranged to the other side of the object, the intensity of the incident X-rays being determined in said field. The detector field 3 generally consists of adjacently arranged single detector cells so that the approximately circular linear configuration with the radiation source 1 as its center is obtained as shown in FIG. 1. The detector field 3 may comprise further rows of detector cells in the direction perpendicular thereto (that is, perpendicular to the plane of drawing) so that a two-dimensional, multi-cell detector matrix is formed. The invention further includes a correction unit 8 for scatter correction of the radiation intensity measured in the detector field 3.

In front of the detector field 3 there may be arranged a further collimator 5 which is capable of reducing the penumbra produced by the first collimator 6. However, because the collimator 5 behind the object also absorbs scattered radiation, it is preferably dispensed with in the context of the present invention.

The X-rays that are incident on the detector field 3 consist on the one hand of direct radiation which reaches the detector 3 without having interacted with the object 2 or the vicinity of the X-ray source 1. A part of the photons is absorbed in the irradiated object and hence is absent in the direct radiation. The degree of absorption is dependent on the length of the path of the beam through the object and on the material composition along this path. This absorption contains the information required for the formation of the computed tomogram.

Furthermore, the interaction between the X-rays and the matter gives rise to scattering processes; essentially three different interaction processes are of relevance in the energy range of from 10 to 140 keV that is of interest for diagnostic purposes: the photo absorption (with subsequent K fluorescence emission), the coherent scattering and the incoherent scattering. The latter two processes do not destroy the interacting photon but change its direction.

A part of the scattered photons also reaches the detector field 3 where these photons contribute to the intensity signal measured in a detector cell. However, because the detector cell cannot determine whether the photon originates from a scattering process or arrives directly from the radiation source 1 (primary photon), the scattered photons obstruct exact measurement of the absorption along the direct path to the radiation source. The scattered radiation thus affects the quality that can be achieved by means of the imaging method. Therefore, it is attempted to prevent the incidence of scattered radiation on the detector field 3 by means of anti-scatter grids. Alternatively it is attempted to estimate the effect of the scattered radiation as accurately as possible in order to perform a scatter correction on the measuring data.

The scatter distribution 4 arising is also shown diagrammatically in FIG. 1. It can be seen that the absolute magnitude of the scattered radiation increases at the edges of the irradiated object 2. The ratio of scattered to primary radiation (SPR), however, exhibits its maximum at the center of the projected object 2, because the primary radiation is minimum at that area because of the absorption (see FIG. 3 hereinafter).

Figure 2:
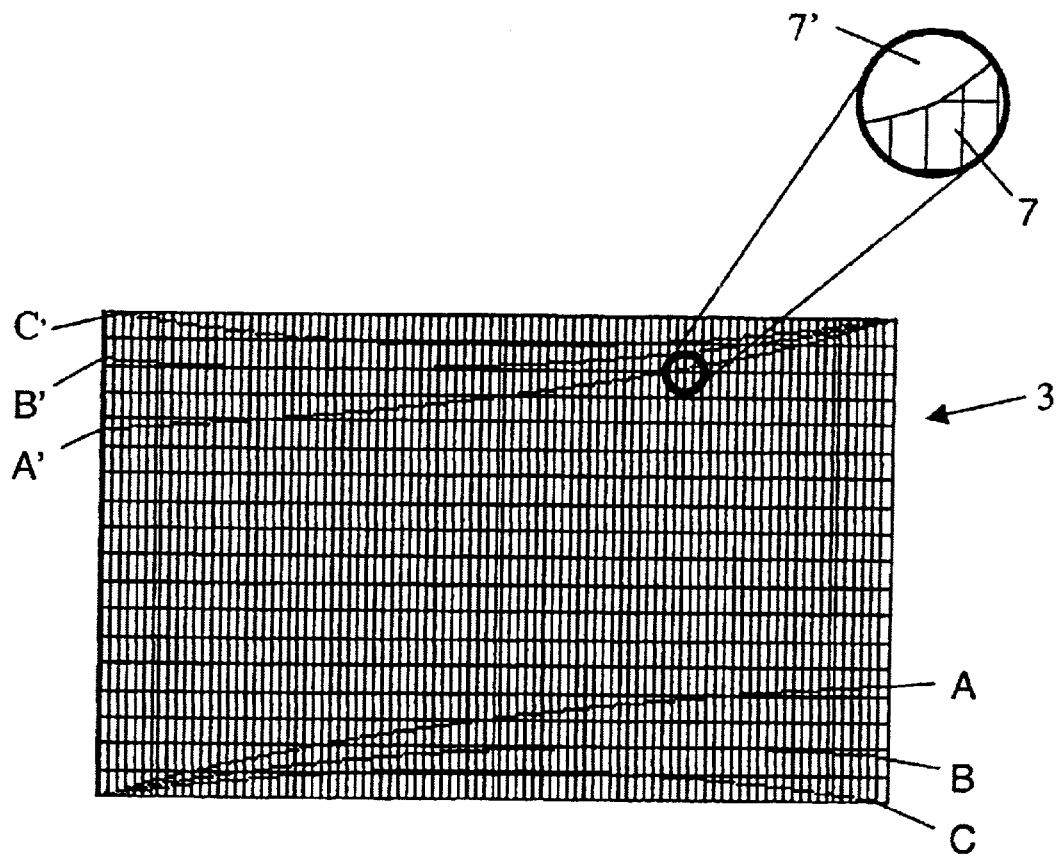
FIG. 2 shows a two-dimensional detector field with regions shielded in different ways.

FIG. 2 shows a two-dimensional detector field 3 in which detector cells 7, 7' are arranged adjacent one another in the form of a matrix in two dimensions. A detector field of this kind is required for a variety of reconstruction algorithms where the detector field 3 is asymmetrically irradiated. Algorithms of this kind, for example the so-called Pi line algorithm or the PHI method, require a special shape of the detector field which is not bounded at right angles but usually has sides that are bounded by curved lines. Because the exact shape of the required detector surface is dependent on the acquisition parameters, it is preferably flexibly defined by the collimators 5, 6 arranged near the radiation source and/or near the detector field. Collimation is necessary to avoid unnecessary irradiation of the patient and hence minimize the radiation dose.

In FIG. 2 the shielded or directly irradiated detector surfaces, as they occur for various algorithms, are represented by their edges A, B, C, A', B', C'. For example, the surface that lies between the curved lines A and A' is irradiated directly in the case of a method where the measuring arrangement, consisting of the radiation source and the detector surface, is helically rotated around the patient.

As is also shown in FIG. 2, numerous cells 7' of the detector field on which the algorithms are based are not exposed to direct irradiation. It may be that a shadow zone appears in the edge zone of the directly irradiated detector field; such a shadow zone is due to the finite dimensions of the radiation source. This shadow zone can be limited or minimized, however, by collimators arranged near the detector. In any case, the arrangements include detector cells 7' which can be struck exclusively by scattered radiation. The signal from these detector cells 7' that are shielded from direct irradiation and are exposed only to scattered radiation is used to perform a scatter correction using correction unit 8 in accordance with the invention for the cells 7 which are situated in the directly irradiated region of the detector field 3. In comparison with the subtraction of a constant scatter background, the direct measurement of the scattered radiation offers the advantage that it is not estimated but measured separately for the relevant situation and that it yields a spatially resolved distribution along the axis of the detector field 3. As can be seen from the enlarged detail of FIG. 2, the measured intensity in a directly irradiated detector cell 7 can be corrected by way of the scattered radiation variable that is measured in the nearest shielded detector cell 7'. Alternatively, a parameterized, overall mathematical model for the scatter distribution can be adapted to the measured values so that the scatter correction can be determined by means of the model. It is to be noted that the model may also consist of a simulation of the scattering of virtual photons.

Figure 3:
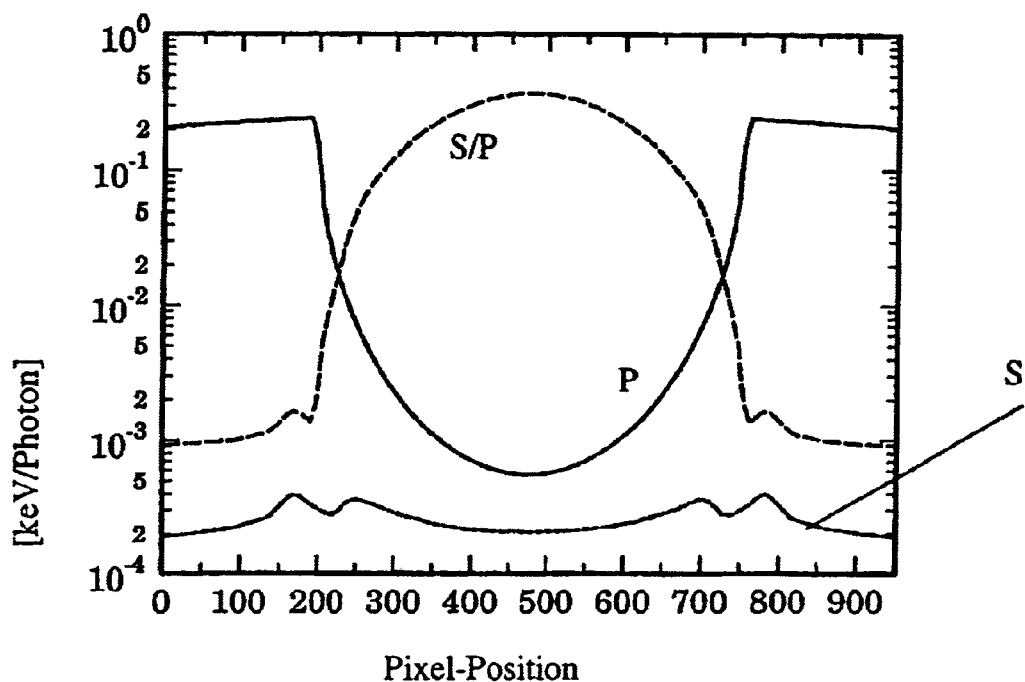
FIG. 3 shows primary radiation and scattered radiation on a spherical test body.

FIG. 3 shows simulated values for the primary radiation P and the scattered radiation S obtained for a water sphere of a diameter of 30 cm while utilizing an X-ray beam of 60 keV. The pixel position of the detector 3 (FIG. 1) is plotted on the horizontal axis and the energy flow density (in keV per photon) is plotted on the vertical axis. The solid curve P represents the measured intensity of the primary (direct) photons; this intensity decreases to a minimum in the direction of the center of the detector field. This variation can be explained on the basis of the fact that the absorption of the primary photons increases continuously because the path length increases from the edge to the center of the sphere.

The curve S in the form of short dashes represents the intensity of the scattered photons. The curve in the form of longer dashes represents the ratio S/P of the primary radiation to the scattered radiation. It appears that this ratio reaches a maximum at the center below the sphere. Therefore, if a constant scattered radiation background is assumed and subtracted from the signal of the primary photons, as is done in customary methods, a so-called "pocket" effect occurs in the reconstructed image. This means that the scattered radiation is overestimated in the direction of the edges of the object, thus giving rise to overestimation of the absorption. The edges of the object are thus reconstructed optically too densely in comparison with the center of the object. This leads to disturbing pockets or bands in the reconstructed cross-section.

Figure 4:
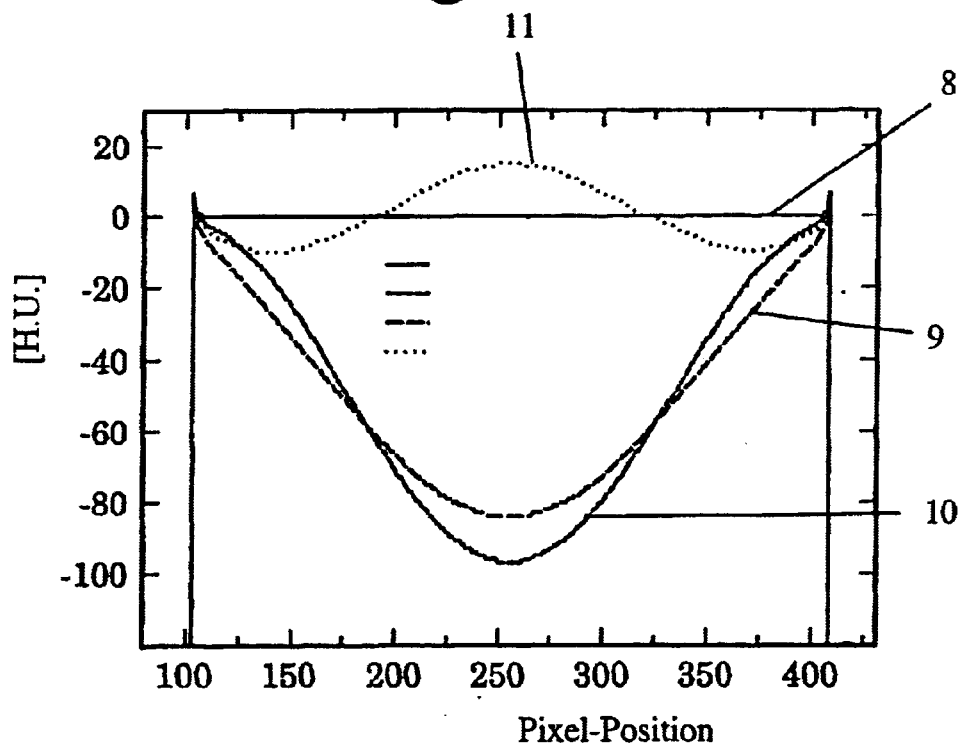
FIG. 4 shows the cross-sectional image of the test body that is derived from the data of FIG. 3 and the effect of various methods for scatter correction.

FIG. 4 shows a reconstruction of the cross-section of the sphere whose simulated measurement is shown in FIG. 3. In the absence of scattered radiation the solid line 8 which corresponds to a constant density that is homogeneous throughout the sphere should be obtained. The line 10 that is formed by short dashes shows a shift, assuming a constant scatter background, with a ratio of scattered to primary radiation of 37% for the smallest primary radiation signal. The curve 9, formed by longer dashes, shows the result of scattered radiation calculated in computer simulations with a maximum ratio of scattered radiation to primary radiation of 37%. The dotted line 11 represents the resultant reconstruction when the constant scatter shift is subtracted from the simulated background. The deviations still present are indicative of a scatter correction that is too simple.

The computer simulation of the scattered radiation is preferably performed while utilizing a simulation model for the photon interactions that is based on the Monte Carlo method. From the simulations a set of calculated scatter distributions can be calculated for a plurality of radiation sources and beam parameters for different zones of the human body, said distributions corresponding to typical tomography scenarios and being usable for drafting a look-up table. Notably the following effects can be taken into account for the calculation of the scatter processes:

a) the interaction between the X-rays and the patient and the patient table, b) the interaction with the mechanical environment (collimators, anti-scatter grids, detector cover etc.), c) the energy deposition of the radiation in the scintillator, and d) backscatter effects of transmitted photons.

Differences in the size of patients can also be taken into account by way of scaling factors. Possible differences between the simulations and real measurements, moreover, can be compensated by measured normalizing factors. Very accurate correction of the scatter can be performed by utilizing a computer simulation providing the necessary information concerning the scanning scenario. The calculated results can be stored in a look-up table for scatter distribution values that is typically implemented in special hardware such as, for example a DSP correction board or a fast PC for real-time correction.

Figure 5:
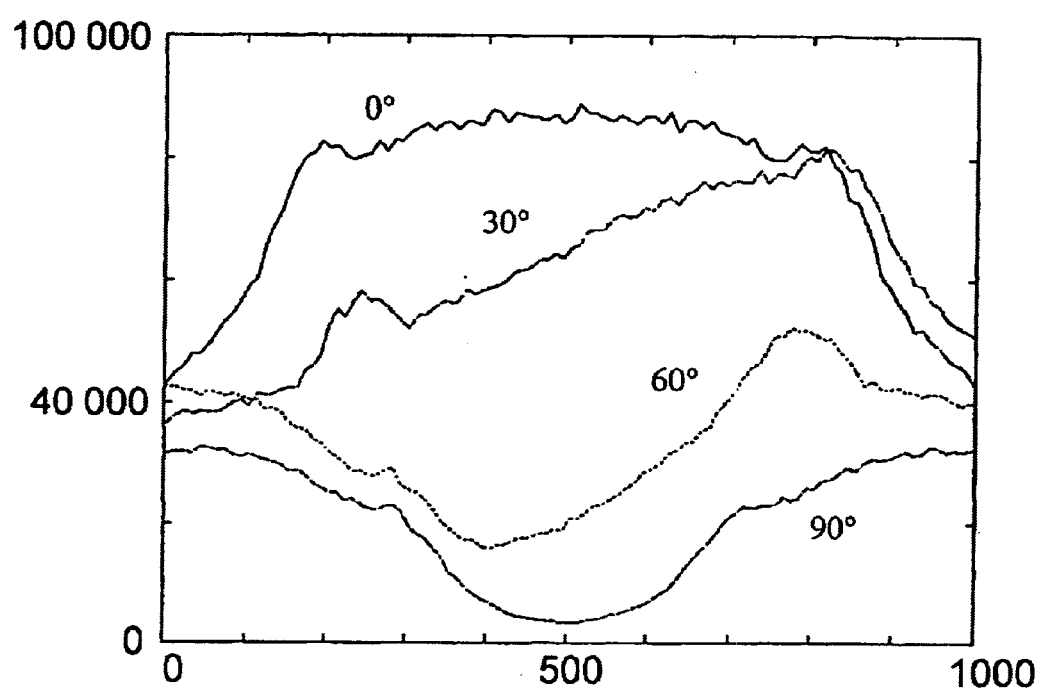
FIG. 5 shows simulated curves for the scatter background on an elliptical object for a rotation of 0°, 30°, 60° and 90° around the object.

FIG. 5 shows simulated curves of the scatter background for an ellipsoidal object containing two bone inclusions (relative units of the radiation intensity on the y-axis, detector pixel position on the x-axis). Apart from statistical fluctuations, the curves show the smooth (low-frequency) behavior of the scatter background. The individual curves correspond to a rotation of 0°, 30°, 60° and 90° about the object, the longitudinal axis of the object being projected onto the detector for 0°.

What is claimed is:

1. A method of forming a computed X-ray tomogram of an object (2) which is irradiated in a measuring arrangement, characterized in that the measuring arrangement comprises of an X-ray source (1) and a detector field (3), radiation intensity measured in the detector field (3) being subjected to scatter correction, the detector field (3) being a two-dimensional multi-cell field, a part of which that is not bounded at right angles is shielded from direct irradiation by the X-ray source, and the radiation intensity in the shielded part of the detector field is measured and used for scatter correction of the measuring values in the directly irradiated part of the detector field.

2. A method as claimed in claim 1, characterized in that the shielded part of the detector field is bounded at least partly by curved lined (A, A'; B, B'; C, C').

3. A method as claimed in claim 2, characterized in that only cells (7') of the shielded part of the detector field that are completely shielded are taken into account for the scatter correction.

4. A method as claimed in claim 3, characterized in that the radiation intensity that has been averaged over at least two cells (7') of the shielded part of the detector field (3) is used for the scatter correction of the measuring values in the directly irradiated part of the detector field.

5. A method as claimed in claim 4, characterized in that from a point (7) of the directly irradiated part of the detector field there is subtracted the radiation intensity which results from an interpolation or extrapolation of all radiation intensities or a part of all radiation intensities measured in the shielded part of the detector field, notably the radiation intensity measured in the nearest cell (7') or the average intensity measured in at least two of the nearest neighbor cells of the shielded part of the detector field.

6. A method as claimed in claim 5, characterized in that the measuring arrangement is displaced along a helical path around the axis of the object (2).

7. An X-ray computed tomography apparatus comprising:
a measuring arrangement with an X-ray source (1), a detector field (3) and shielding means (5, 6) for the detector field, wherein the detector field (3) being a two-dimensional multi-cell field, a part of which that is not bounded at right angles is shielded from direct irradiation by the X-ray source; and a correction unit for scatter correction of radiation intensity measured in the detector field, wherein the correction unit is coupled to the shielded part of the detector field and is arranged in such a manner that the correction unit utilizes the radiation intensity measured in the shielded part for the scatter correction.

8. A method as claimed in claim 1, characterized in that the cells of the multi-cell field do not all have the same geometrical size.

9. An X-ray computed tomography apparatus as claimed in claim 8, characterized in that the correction unit is coupled to the shielding means (5, 6) in such a manner that the correction unit receives signals concerning the shape and the size of the shielded part of the detector field.

10. A method, notably as claimed in claim 6, for forming a computed X-ray tomogram of an object (2) which is irradiated in a measuring arrangement that consist of an X-ray source (1) and a detector field (3), the radiation intensity measured in the detector field being subjected to scatter correction, characterized in that the results of a computer simulation of the scattering processes are taken into account for the scatter correction.

11. A method as claimed in claim 10, characterized in that the computer simulation is carried out by means of a Monte Carlo simulation of virtual photon paths.

12. A method as in claim 10, characterized in that the computer simulation takes into account the geometry and material properties of the measuring arrangement, of a patient table and of other objects possibly involved in scattering processes.

13. A method as claimed in claim 12, characterized in that the computer simulation takes into account the geometry and the material properties of a model of a patient body in an irradiated zone.

14. A method as claimed in claim 13, characterized in that the results of the computer simulation are adapted to a live patient's body size by multiplication by at least one scaling factor.

15. A method as claimed in claim 14, characterized in that the computer simulation takes into account the interaction between the scatter and the detector field.

16. A method as claimed in claim 15, characterized in that the computer simulation takes into account backscattering from a region that is situated behind the detector field, that is, viewed from the radiation source.

17. A method as claimed in claim 16, characterized in that the results of the computer simulation are stored in a look-up table for various parameters, such as the geometry of the measuring arrangement, the measuring method used, and the object size.

18. An X-ray computed tomography apparatus as claimed in claim 7, characterized in that the cells of the multi-cell field do not all have the same geometrical size.

19. An X-ray computed X-ray tomography apparatus as claimed in claim 18, characterized in that the correction unit includes a memory for storing a look-up table with results of at least one computer simulation.

20. An X-ray computed tomography apparatus as claimed in claim 18, characterized in that the correction unit includes at least one digital signal processor.

* * * * *